(12) United States Patent
Peters et al.

(10) Patent No.: US 11,185,237 B2
(45) Date of Patent: Nov. 30, 2021

(54) CALIBRATION METHODS FOR BLOOD PRESSURE DEVICES

(71) Applicants: Robert Bosch Tool Corporation, Broadview, IL (US); Robert Bosch GmbH, Stuttgart (DE)

(72) Inventors: Christian Peters, Mountain View, CA (US); Thomas Rocznik, Mountain View, CA (US); Seow Yuen Yee, Mountain View, CA (US); Igino Padovani, San Jose, CA (US)

(73) Assignee: Robert Bosch GmbH, Stuttgart (DE)

( * ) Notice: Subject to any disclaimer, the term of this patent is extended or adjusted under 35 U.S.C. 154(b) by 909 days.

(21) Appl. No.: 15/912,952

(22) Filed: Mar. 6, 2018

(65) Prior Publication Data

US 2019/0274553 A1 Sep. 12, 2019

(51) Int. Cl.
| | |
|---|---|
| *A61B 5/0205* | (2006.01) |
| *A61B 5/00* | (2006.01) |
| *A61B 5/026* | (2006.01) |
| *A61B 5/021* | (2006.01) |
| *A61B 5/022* | (2006.01) |
| *A61B 5/024* | (2006.01) |

(52) U.S. Cl.
CPC .......... *A61B 5/0205* (2013.01); *A61B 5/0004* (2013.01); *A61B 5/022* (2013.01); *A61B 5/026* (2013.01); *A61B 5/02108* (2013.01); *A61B 5/743* (2013.01); *A61B 5/024* (2013.01); *A61B 5/02233* (2013.01); *A61B 2560/0223* (2013.01); *A61B 2562/0219* (2013.01)

(58) Field of Classification Search
CPC ... A61B 5/0205; A61B 5/02108; A61B 5/002; A61B 5/0004; A61B 5/026; A61B 5/743; A61B 5/02233; A61B 5/024; A61B 2560/0223; A61B 2562/0219
See application file for complete search history.

(56) References Cited

U.S. PATENT DOCUMENTS

| | | |
|---|---|---|
| 2006/0074322 A1 | 4/2006 | Nitzan |
| 2014/0121546 A1 | 5/2014 | Mills et al. |

(Continued)

FOREIGN PATENT DOCUMENTS

WO 2018/013569 A1 1/2018

*Primary Examiner* — Ryan W Sherwin
(74) *Attorney, Agent, or Firm* — Maginot, Moore & Beck LLP (57) ABSTRACT

A method for calibrating a blood pressure monitoring system includes activating a reference monitor to perform a reference measurement of the blood pressure of a user as part of a calibration process. A wearable sensing device is activated to detect a parameter of user that is correlatable to the user's blood pressure. A processor of the user interface device processes the at least one parameter detected by the wearable blood pressure sensing device with reference to the reference measurement to determine a correlation factor that correlates the at least one parameter detected by the wearable blood pressure sensing device to the blood pressure of the user. The reference measurement includes an inflation phase, a measurement phase and a deflation phase. The processor is configured to only use the at least one parameter detected by the wearable blood pressure sensing device during the measurement phase in determining the correlation factor.

14 Claims, 6 Drawing Sheets

(56) References Cited

U.S. PATENT DOCUMENTS

2017/0042433 A1\* 2/2017 Noh ...................... A61B 5/1118
2017/0332921 A1 11/2017 Zirngibl
2018/0279888 A1\* 10/2018 Wang ................... A61B 5/0002

\* cited by examiner

CALIBRATION METHODS FOR BLOOD PRESSURE DEVICES

TECHNICAL FIELD

This disclosure is related generally to health monitoring devices, and more particularly, to blood pressure monitoring systems and methods for calibrating such systems.

BACKGROUND

Blood pressure (BP) is an important indicator of cardiovascular health and other physiological conditions. Blood pressure may be measured with conventional methods on an infrequent basis in a medical setting. However, there are also needs to measure blood pressure on a more frequent basis and under various conditions outside of the medical setting. For instance, certain blood pressure dynamics, e.g., the non-dipper blood pressure pattern, when a person is sleeping, are of medical importance. Such dynamics are not easily measurable with conventional methods. Moreover, for example, blood pressure variations during daily activities after certain medications are consumed may be used to optimize medical treatments.

Conventional noninvasive methods for measuring blood pressure include oscillometric blood pressure measurement (OBPM) methods and auscultation methods using sphygmomanometer. Both methods require the use of an inflating cuff which can cause discomfort to the user. Other conventional blood pressure measuring methods include tonometry and the volume clamp method. The former requires a trained operator while the latter is also cumbersome and relatively obtrusive in a person's every day routine. As such, these conventional methods are not ideal for blood pressure measurements on a frequent basis and under various conditions, e.g., ambulatory blood pressure measurements (ABPM).

Most cuff-less blood pressure (BP) monitoring systems can only provide a relative but not absolute value. For same applications like stress level monitoring the relative value is sufficient. However to get the absolute value a calibration step is needed. This step must be simple and easy to use. Different techniques are described in the following for a convenient and less error prone calibration step.

The calibration step is very critical for a good estimation of the absolute blood pressure value. The calibration points taken with respect to a reference monitor 16 has to be as accurate and as close to the reality as possible to reflect the current conditions of the blood pressure. Blood pressure changes dynamically and even the reference monitor such as the blood pressure cuff might not capture the whole truth of the blood pressure value.

BRIEF DESCRIPTION OF THE DRAWINGS

FIG. 7 is a graph of an example sensor output of the sensing device over time showing the

DETAILED DESCRIPTION

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to a person of ordinary skill in the art to which this disclosure pertains.

The disclosure is directed to a calibration process, including calibration protocols, calibration methods and algorithms for calibrating non-invasive, cuff-less blood pressure devices. The calibration process enables an accurate estimation of blood pressure values based on reference blood pressure measurements from a reference monitor 16, such as a cuff-based sphygmomanometer. The process of calibration can range from fully automatic to semi-manual to manual calibration protocols. A fully automatic calibration procedure does not require specialist knowledge or interaction from the user whereas semi-manual or manual calibration procedures allow the user to double check the reasonableness of the calibration points and the user can take action to assure that the calibration is performed under control conditions (e.g. no movements, correct placement of reference monitor 16, etc.)

Figure 1:
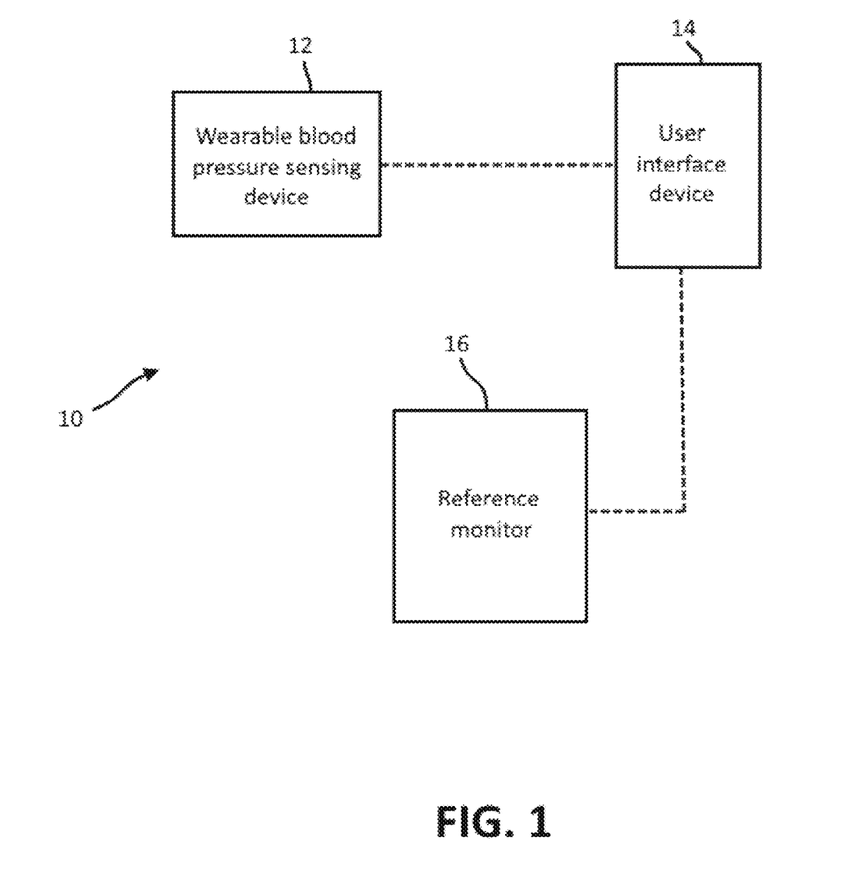
FIG. 1 is a schematic block diagram of a blood pressure monitoring system in accordance with the present disclosure.
Figure 2:
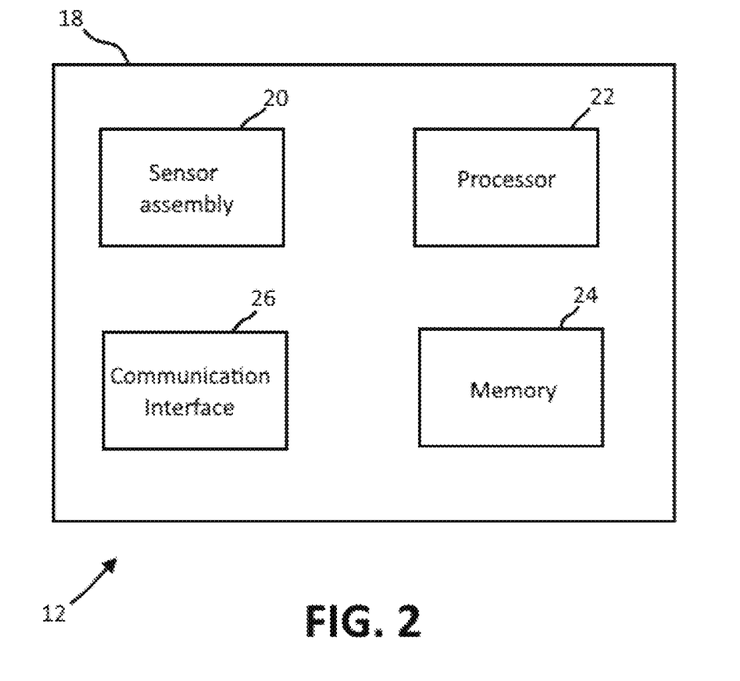
FIG. 2 is a schematic block diagram of a sensor assembly of the blood pressure monitoring system of FIG. 1.

FIG. 1 is a schematic depiction of a blood pressure monitoring system 10 in accordance with the present disclosure. The blood pressure monitoring system 10 includes a wearable blood pressure sensing device 12, a user interface device 14 and a reference monitor 16. The wearable blood pressure sensing device 12 is a device that is configured to be attached or held in place on a user's body at a location to detect a physical parameter of the user's body that can be correlated to blood pressure. An embodiment of a wearable blood pressure sensing device 12 is depicted in FIG. 2. As depicted, the wearable blood pressure sensing device 12 includes a housing 18, a sensor assembly 20, a processor 22, a memory 24 and a communication interface 26.

The housing 18 may be provided to encapsulate at least one or more of the sensing assembly 20, the processor 22, the memory 24, and the communication interface 26. In one embodiment, the housing 18 may be formed from a thin film material that allows the target to stretch, bend, twist, squeeze, fold, expand, or combinations thereof and may be either worn by the user, adhered to the user's body, or implanted into the user's body. As some examples, the wearable blood pressure sensing device 12 may be a patch, a necklace, a chest strap, a pendant, or any suitable device.

The sensor assembly 20 is configured to detect at least one parameter of the user that can be correlated to blood pressure. The sensor assembly 20 may utilize any suitable type of sensor or device to detect the at least one parameter. In one embodiment, the sensor assembly 20 includes at least one accelerometer which is configured to detect a mass transit time related to blood flow in the user's circulatory system (explained in more detail below). As used herein, the term "Mass Transit Time (MTT)" refers to the time interval between the start of the blood ejection from the heart to the time where blood turns at the arches of the aorta or any other specific locations where the change in the blood flow can be detected. It is not a pulse transit time because not the pulse is detected but the transit of the mass of blood and the resulting impulse of the mass movement to the torso of the body. Therefore, it is called mass transit time and not pulse transit time. Other start and end events can also be used to measure MTT.

For more details regarding mass transit time, reference is made to U.S. patent application Ser. No. 15/834,686 to Yee et al. entitled "Blood Pressure and Cardiac Monitoring System and Method Thereof", the disclosure of which is hereby incorporated herein in its entirety. In addition to mass transit time, the sensor assembly 20 may include at least one sensor, such as an accelerometer, for detecting heart rate of the user. In this embodiment, the blood pressure sensing device 12 may be configured as a patch which is applied to the sternum of the user. Since bones can transfer the body movement due to cardiac activities with less damping effects than muscles, the sensor assembly 20 is able to detect the signal that is less affected by motion artifacts. In another embodiment, the sensor assembly 20 may be placed on any location of the body proximal to the sternum of the target. In yet another embodiment, the sensor assembly 20 is configured to detect the time interval between heart contraction and blood flow. In alternative embodiments, the sensor assembly 20 may be configured to detect any parameter that maybe correlated to blood pressure, such as electrocardiogram (ECG) sensors, photoplethysmorgram (PPG) sensors, seismocardiogram sensors (SCG), ballistocardiogram (BCG) sensors, motion sensors, optical sensors, transducers, Doppler ultrasonic transducers, radar, acoustic sensors, electrodes, an ECG sensor, a target orientation sensor, a sonar sensor, a thermal sensor, an environmental sensor, or any suitable sensor or transducer The sensor assembly 20 is configured to output sensor signals indicative of mass transit time and heart rate to the processor. The processor 22 may be of any type, including but not limited to a microprocessor, a microcontroller, a digital signal processor, or any combination thereof. The processor 22 is communicatively coupled to the memory which is used by the processor 22 to store data, such as computer-readable instructions that, when executed by the processor, causes the processor 22 to control the sensor assembly 20 and communication interface in accordance with the calibration methods and procedures described herein. The memory 24 may include any transitory, non-transitory, volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

The communication interface 26 enables data to be transferred between the processor 22 and the user interface device 14 in the form of signals which may be, for example, electronic, electromagnetic, optical, or other signals capable of being received by the communication interface. The communication interface 26 may be implemented using any suitable hardware and/or software and may be configured to use any suitable communication protocol. In one embodiment, the communication interface comprises a wireless transceiver configured to implement a wireless communication protocol, such as Bluetooth™. In operation, the processor 22 is configured to receive commands from the user interface device 14 and to send data (e.g., sensor output) to the user interface device 14 via the communication interface.

Figure 3:
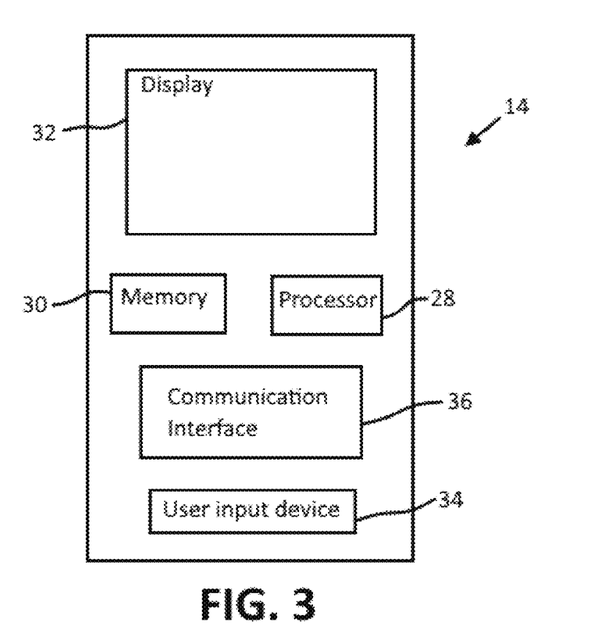
FIG. 3 is a schematic block diagram of a user interface device of the blood pressure monitoring system of FIG. 1.

Referring to FIG. 3, the user interface device 14 comprises a portable, handheld electronic device which is configured to interface with the wearable blood pressure sensing device 12 and to enable a user to interact with the blood pressure monitoring system in meaningful ways. The user interface device 14 may comprise a processor 28, a memory 30, a display 32, an input device 34 and a communication interface 36. The user input device 34 comprises one or more hardware or software implemented buttons, keys, and the like that enable the user to input data and make selections. The processor 28 is communicatively coupled to the memory 30 which is used by the processor 28 to store data, such as computer-readable instructions that, when executed by the processor, enable the processor 28 to operatively control the display 32 and communication interface 36 to implement certain steps of the calibration methods and procedures described herein and based at least in part on input received via the user input device. The memory 30 may include any transitory, non-transitory, volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

The user interface device 14 may comprise a smartphone, tablet, laptop computer, desktop computer, or a dedicated electronic device. In one embodiment, blood pressure monitoring procedures and blood pressure device calibration procedures are implemented as software applications, e.g., "apps", on the user interface device 14. Apps comprise programmed instructions that may be stored in the memory and executed by the processor when selected by a user via the input device. The communication interface 36 may be implemented using any suitable hardware and/or software and may be configured to use any suitable communication protocol, such as Bluetooth™, to enable communication with the wearable blood pressure sensing device 12 and, in some embodiments, the reference monitor 16. Other communication protocols that may be implemented include Zigbee, 802.15.4, WiFi, NFC, Z-wave and the like.

The reference monitor 16 may be any suitable device capable of providing accurate reference blood pressure measurements, e.g., systolic and diastolic blood pressure, for calibrating the blood pressure monitoring system. For example, the reference monitor 16 may comprise a cuff-based sphygmomanometer, a cuff-based automatic blood pressure monitoring device, hemodynamic monitoring system such as Finapres or pulse transit time monitors or echocardiogram, or implantable blood pressure monitors.

The blood pressure monitoring system 10 may be provided as a retro-fit system or an all-in-one system. In a retro-fit system, the reference monitor 16 is provided as a separate component from the wearable blood pressure sensing device 12 and user interface device 14. As such, the reference monitor 16 and the user interface device 14 are not able to communicate or pass data without some form of manual intervention from the user.

For a retro-fit system, the user is responsible for getting the reference blood pressure measurements entered into the user interface device 14 during the calibration process. This can be performed in different ways. For example, the user may simply enter the blood pressure values into the user interface device 14 via the user input device. This is a manual implementation of calibration process. In other embodiments, the user interface device 14 may be configured to receive the reference blood pressure values by scanning an image taken of the reference monitor 16 by the user using a camera of the user interface device 14. This is a semi-manual implementation of the calibration procedure.

In an all-in-one version of the blood pressure monitoring system, the wearable blood pressure sensing device 12, the user interface device 14 and the reference monitor 16 are configured to work together without requiring manual intervention of the user. As such, the reference monitor 16 includes necessary components, such as a processor, memory, and communication interface, to enable the reference monitor 16 to receive commands from the user interface device 14 and to transmit reference blood pressure measurements to the user interface device 14 for implementing a fully automatic calibration procedure.

Figure 4:
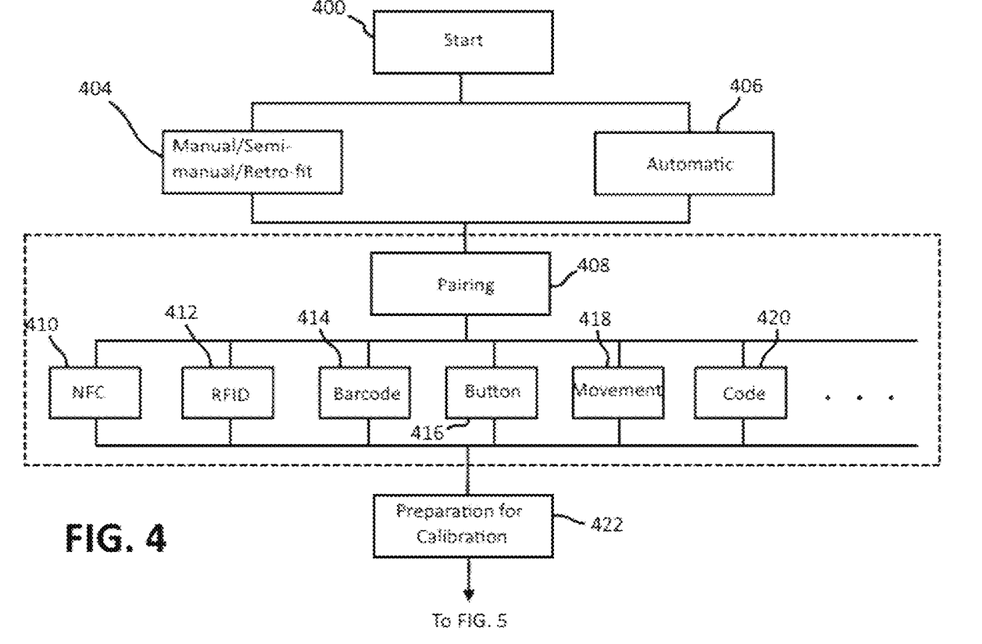
FIGS. 4-6 depict a flow chart of a calibration procedure for the blood pressure monitoring system of FIG. 1.
Figure 5:
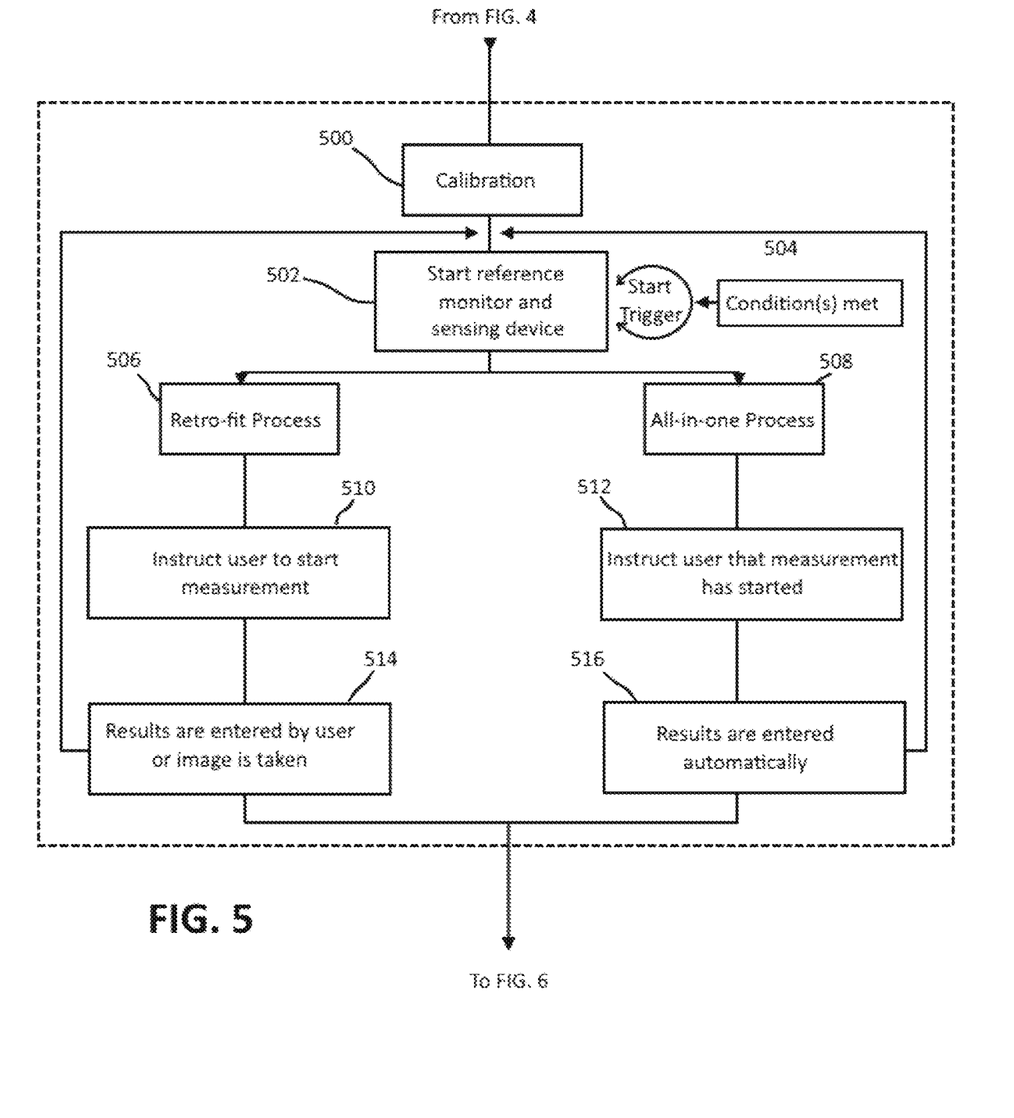
Figure 6:
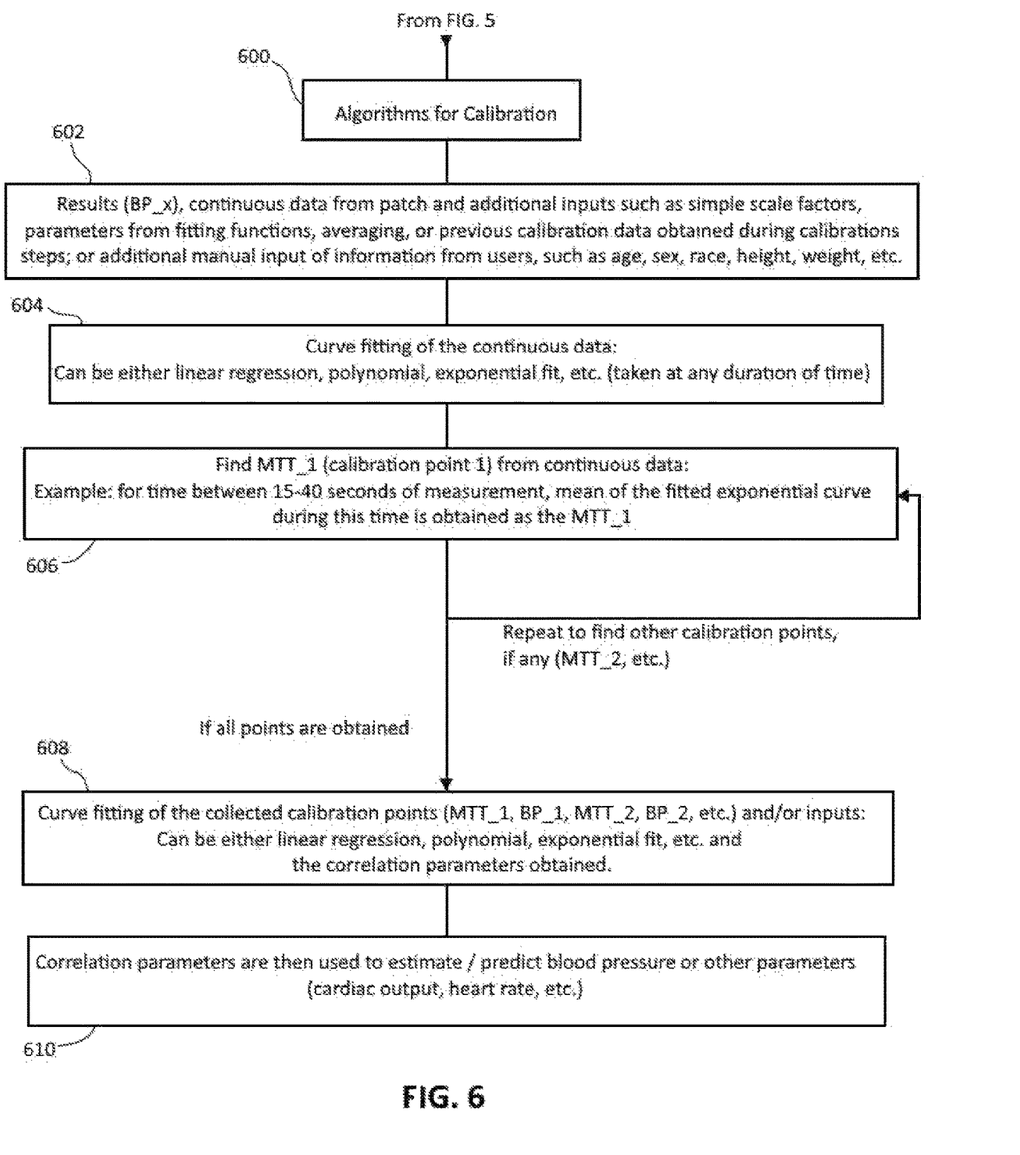

FIGS. 4-6 depict a flowchart of a calibration procedure in accordance with the present disclosure. The calibration process may be initiated by a user via an input or selection made by the user via the user input device (Start, block 400). Once initiated, the user interface device 14 is configured to provide instructions to the user to guide the user through the entire calibration procedure. The instructions may be provided visually and/or auditorily. Programmed instructions for execution by the processor for providing the instructions to the user may be stored in the memory of the user interface device 14. As discussed below, the procedure followed and therefore the instructions given can vary depending on whether the system is a retro-fit system (block 404) or an all-in-one system (406).

The first step performed after the calibration procedure has been initiated is to determine whether the user interface device 14 is communicatively coupled, or paired, to the wearable blood pressure sensing device 12 (block 408). For example, a pairing function in the calibration app may be selected to start the pairing process. Depending on the available hardware of the user interface device 14 different methods for pairing may be used, including near field communication (NFC) (block 410), radio-frequency identification (RFID) (block 412), code (blocks 414, 420), button (block 416), movement (428) and the like. For NFC and RFID, the wearable blood pressure sensing device 12 is brought into close contact with an NFC reader or an RFID reader, respectively, of the user interface device 14 to automatically start the pairing process. The wearable user interface device 14 may be provided with a barcode, or an alphanumeric code, that can be scanned by the user interface device 14 to initiate the pairing process. The pairing process may be initiated by pressing a button provided on the wearable user interface device 14. Knocking, bumping or other synchronic movements (e.g., shaking, tapping, etc.) of the wearable blood pressure sensing device 12 and the user interface device 14 may be used to initiate the pairing process. In this case, the time correlation between the impacts or movements which are measured at both devices is used to start the pairing. Of course, the pairing process may be initiated automatically when the user interface device 14 and wearable blood pressure sensing device 12 are powered on and/or when the wearable blood pressure sensing device 12 is placed on skin.

Before or after pairing, the sensing device 12 is placed on the body of the user. Instructions may be provided to the user via the user interface device 14 as to where the sensing device 12 should be placed (block 422). The reference monitor 16, e.g., the cuff, is also placed in the appropriate location on the user's body (before or after pairing) (block 422).

Referring to FIG. 5, once the sensing device 12 and the reference monitor 16 are in place and the sensing device 12 has been paired with the user interface device 14 (which may be confirmed by the user on the user interface device 14), calibration is initiated (block 500). Reference measurements are performed during the calibration process. Each measurement generates a calibration point. One, two or more calibration points may be used for the calibration procedure (as discussed below). Instructions provided on the user interface device 14 may guide the user through the procedure.

For the first measurement point, the user is instructed via the user interface device 14 to perform a certain activity which influences the blood pressure (stabilizes, increases or decreases). The activity could be laying down or sitting still to stabilize the blood pressure at a low level or performing some activity to increase or decrease blood pressure, such as exercising (e.g. squatting, running, walking at a fast speed, alternating between sitting and standing, etc.), changing positions and postures (e.g. sitting versus lying down, sitting with head up versus sitting with head on the lap, etc.), intake of food or drugs or hormones, or the like.

The sensing device 12 may include sensors for detecting and monitoring the movement of the user during this time which can be communicated to the user interface device 14. The user interface device 14 instructs the user to start the measurement procedure (block 502) when predetermined conditions have been met (block 504). For example, the user interface device 14 may instruct the user to initiate the measurement procedure after a predetermined time has elapsed or by monitoring other parameters such as the heart rate of the user. Heart rate may be determined using a sensor of the sensor assembly 20 of the sensing device 12 or by using a separate device or hand measurement.

For a retro-fit monitoring system (block 506), the user interface device 14 instructs the user to activate the reference monitor 16 to perform a reference blood pressure measurement and to indicate the start of the reference blood pressure measurement on the user interface device 14 (block 510). For all-in-one monitoring systems (block 508), the user interface device 14 and reference monitor 16 are able to communicate with each other automatically. Therefore, the user does not need to activate the reference monitor 16 manually as the user interface device 14 can transmit commands to the reference monitor 16 to activate the reference monitor 16 to being a reference measurement. The user interface device may indicate that the measurement procedure has started (block 512).

During the measurement, the user should minimize any movement, and hold his/her positions stationary. For example, the positions can be either supine position or sitting with back straight position. This should last for a short duration (<2-10 mins) depending on the need to achieve a desired accuracy. The position and movement of the user can be detected and monitored during the measurement by the sensor assembly 20 of the sensing device 12. If an incorrect position and/or too much movement is detected during the measurement, the user interface device 14 may instruct the user to restart the measurement step. The measurement step may be aborted and/or restarted automatically based on the sensor input or manually by the user.

The sensing device 12 continuously detects the parameter(s) of the user correlatable to blood pressure during and after the reference measurement. After the reference measurement has been completed, the results of the measurement, such as systolic, diastolic blood pressure and heart rate, must be transferred into the user interface device 14. For retro-fit systems, this can be done by the user by manually entering the results or using a camera of the user interface device 14 to capture an image of the results (block 514). The user interface device 14 will analyze the image and automatically readout the results. Any suitable method of transferring the results of the reference measurement to the user interface device 14 may be used. This ends the calibration process for a one calibration point measurement. For all-in-one systems, the reference monitor 16 can automatically transfer the reference measurements to the user interface device 14 via the communication link (block 516).

In case of a two or more calibration point measurement, the user interface device 14 instructs the user to begin a subsequent reference measurement procedure. For the subsequent reference measurement procedure, the blood pressure of the user should be different, e.g., higher or lower, compared to the first measurement. To accomplish this, the user is instructed to perform a certain activity to influence the blood pressure in a desired manner such that the user's blood pressure is higher or lower relative to the previous measurement. After that, the user interface device 14 instructs the user to activate the reference monitor 16 to perform the subsequent measurement and to indicate the start of the subsequent measurement on the user interface device 14. Once the reference measurement has been completed, the results of the measurement are transferred to the user interface device 14. This process may be repeated until a desired number of reference measurements and calibration points have been generated.

Referring to FIG. 6, after the desired number of calibration points has been generated, the one or more calibration points are used by the processor of the user interface device 14 to calculate the absolute blood pressure based on the output of the sensors of the sensing device 12. Programmed instructions on the user interface device 14 may be configured to cause the processor to implement a suitable algorithm for calculating the absolute blood pressure (block 600).

The algorithm can be a simple scale factor, a fitting function, averaging or anything else. The algorithm may also be take into consideration previous calibration results or any kind of calibration correction factors (such as age, sex, race, height, weight, etc.) (block 602). Calibration correction factors may be entered by the user into the user interface device 14 in response to queries provided to the user. Afterwards the user interface signals to the user that the wearable sensing device 12 is calibrated and ready to use.

Figure 7:
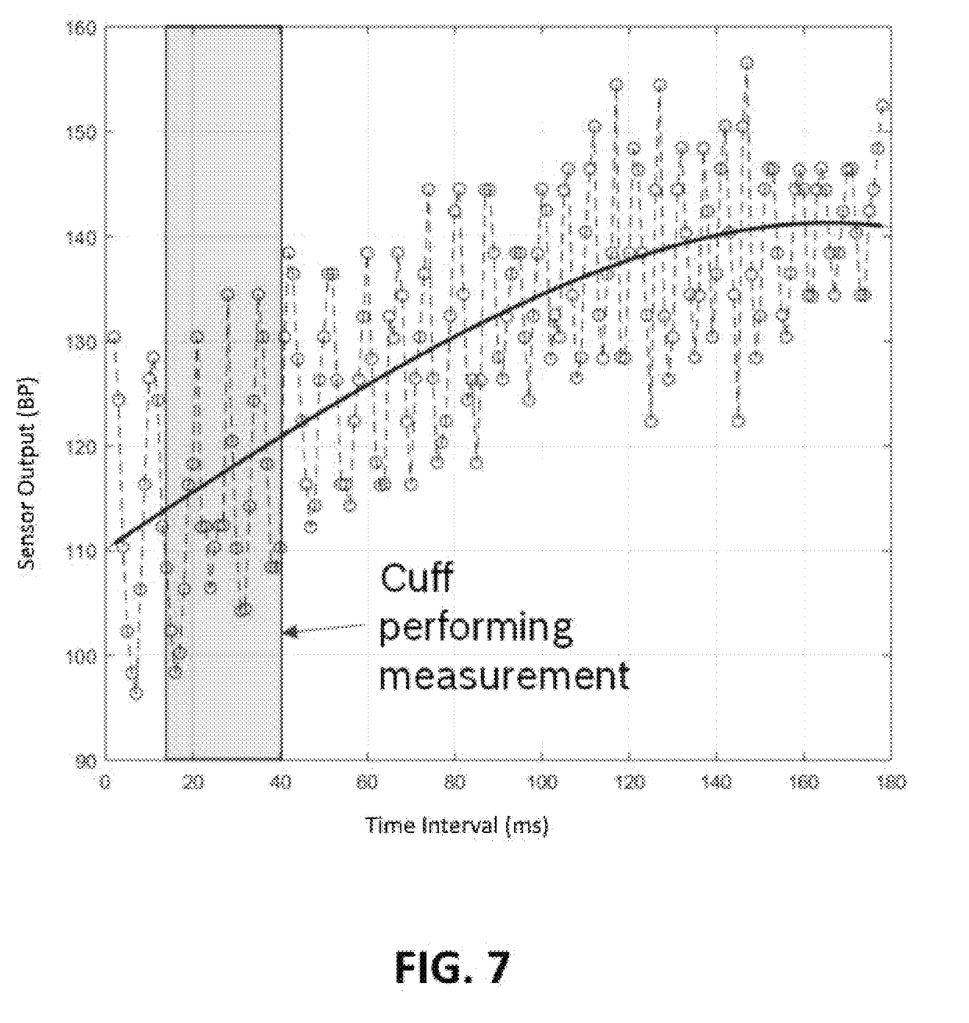

When a reference blood pressure measurement is started as indicated by the user on the user interface device 14, the user interface device 14 commands the wearable sensing device 12 to begin transmitting sensor output to the user interface device 14. FIG. 7 depicts a graph showing results of blood pressure measurements using the sensing device over time. Although the sensing device 12 and the reference monitor 16 measurements are started at the same time, in reality, the reference monitor 16 takes, for example, around 15 seconds or more to inflate the cuff. The actual reference measurement takes place, for example, approximately 15-40 seconds after the reference monitor 16 is activated (indicated by the shaded area in the graph of FIG. 7), at which point the cuff deflates. Depending on the reference monitor used and the BP of the person, the actual measurement duration can varies and the algorithm has to be adapted accordingly. The reference measurement includes an inflation phase, a measurement phase and a deflation phase. The processor is configured to only use the sensor output during the measurement phase (shaded area of graph) in determining the correlation factor.

In addition, the blood pressure of the user during the measurement, especially during the inflation phase, may be more susceptible to changes depending on the event/activity performed by the user right before the measurement is initiated. Also nonphysical effects, such as emotional stress, can influence the blood pressure during measurement time. Therefore, in order to take into account the actual state of a person's blood pressure for high calibration accuracy, the blood pressure calibration algorithm takes into consideration the actual state of the reference monitor 16 by omitting the sensor output of the sensing device 12 during the inflation phase of the measurement procedure.

The time required for the reference monitor 16 to reach a state at which the measurement is actually started and the duration for achieving a measurement for a particular reference monitor 16 are taken into account during the calibration process by omitting the sensor output from the sensing device 12 during this time. The time frame required for the reference monitor 16 to perform a measurement depends on the cuff and on the blood pressure of the subject. This time/duration may be entered into the user interface device 14 by the user for use by the processor in determining when to activate the wearable sensing device 12 and/or when to begin monitoring the output of the sensing device 12. For all-in-one systems or automatically coupled reference monitor 16 and sensing device 12, the time duration for the reference monitor 16 is determined automatically without needing any input from the user. In addition, fitting function and averaging methods can be used for calibration. For example, fitting functions can include exponential functions, linear functions, polynomial functions and the like (block 604).

Next, for calibration purposes, averaging methods or curve fitting methods are used to obtain a blood pressure value which correlates to the value measured by the reference monitor 16. For this example, the mean of the fitted exponential function from the duration of 15-40 seconds of the reference measurement is calculated and this value is used to correlate with the reference blood pressure value from the reference monitor 16. For the first calibration point, this mean value is called MTT_1 and the reference monitor 16 value is called BP_1. Here, MTT is Mass Transit Time and BP is Blood Pressure or Systolic Blood Pressure (block 606). These steps may be repeated to obtain a desired number of calibration points based on new measurements which will be labeled MTT_2 and BP_2, MTT_3 and BP_3 and so on.

After the calibration point's values are collected, another curve fitting function/algorithm is used to obtain the correlation relationship between the sensing device 12 blood pressure values (MTT time interval) with the blood pressure values from the reference monitor 16 (block 608). Correlation parameters may then be used to estimate/predict blood pressure or other parameters(cardiac output, heart rate, and the like) (block 610). The fitting function can vary from linear regression with single parameter with constants such as BP=a*MTT_time_interval+b, where a and b are constants obtained from fitting, to linear regression with multiple parameters with constants such as BP=a*MTT_time_ interval+b*HR+c, where HR is heart rate and a, b, and c are constants. Other parameters can also be used in replacement or in addition to heart rate (HR), such as previous calibration results or any kind of calibration correction factors (such as age, sex, race, height, weight, etc.). In these examples, it has been assumed that the parameters influence the blood pressure linearly. In the case where the influence is non-linear, other fitting methods such as exponential, power or polynomial functions can be used or machine learning algorithms and methods can be used.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method for calibrating a blood pressure monitoring system, the method comprising:

communicatively coupling a user interface device with a wearable blood pressure sensing device, the wearable blood pressure sensing device being placed on a user's body and configured to detect at least one parameter of the user's body that is correlatable to a blood pressure of the user;

activating a reference monitor to perform a reference measurement of the blood pressure of the user as part of a calibration process;

using the user interface device to activate the wearable blood pressure sensing device to detect the at least one parameter while the reference monitor performs the reference measurement, the wearable blood pressure sensing device communicating the detected parameter to the user interface device during the reference measurement;

transferring the reference measurement to the user interface device after the reference measurement has been completed; and using a processor of the user interface device to process the at least one parameter detected by the wearable blood pressure sensing device with reference to the reference measurement to determine a correlation factor that correlates the at least one parameter detected by the wearable blood pressure sensing device to the blood pressure of the user;

wherein the reference measurement includes an inflation phase, a measurement phase and a deflation phase, and wherein the processor of the user interface device is configured to only use the at least one parameter detected by the wearable blood pressure sensing device during the measurement phase in determining the correlation factor, wherein the at least one parameter includes mass transit time of a blood flow of the user.

2. The method of claim 1, wherein the wearable blood pressure sensing device includes at least one accelerometer for detecting the mass transit time.

3. The method of claim 1, wherein the at least one parameter further includes a heart rate of the user.

4. The method of claim 1, wherein the reference monitor comprises an inflatable cuff.

5. The method of claim 1, wherein the user interface device is communicatively coupled to the reference monitor, and wherein the reference measurement is automatically communicated to the user interface device by the reference monitor when the reference measurement is completed.

6. The method of 1, wherein the measurement is manually entered into the user interface device by the user.

7. The method of claim 1, wherein the user interface device comprises a smartphone or a tablet.

8. The method of claim 1, wherein the user interface device provides instructions to the user to guide the user through the calibration process.

9. A method for calibrating a blood pressure monitoring system, the method comprising:

communicatively coupling a user interface device with a wearable blood pressure sensing device and a reference monitor, the wearable blood pressure sensing device being placed on a user's body and configured to detect at least one parameter of the user's body that is correlatable to a blood pressure of the user, the reference monitor being configured to measure a blood pressure of the user;

using the user interface device to activate the reference monitor to perform a reference measurement of the blood pressure of the user and to activate the wearable blood pressure sensing device to detect the at least one parameter during the reference measurement, the at least one parameter detected by the wearable blood pressure sensing device being communicated to the user interface device;

automatically communicating the reference measurement to the user interface device from the reference monitor after the reference measurement has been completed; and using a processor of the user interface device to process the at least one parameter detected by the wearable blood pressure sensing device with reference to the reference measurement to determine a correlation factor that correlates the at least one parameter detected by the wearable blood pressure sensing device to the blood pressure of the user, wherein the at least one parameter includes mass transit time of a blood flow of the user.

10. The method of claim 9, wherein the reference measurement includes an inflation phase, a measurement phase and a deflation phase, and wherein the processor of the user interface device is configured to only use the at least one parameter detected by the wearable blood pressure sensing device during the measurement phase in determining the correlation factor.

11. The method of claim 9, wherein the user interface device comprises a smartphone or a tablet.

12. The method of claim 9, wherein the wearable blood pressure sensing device includes at least one accelerometer for detecting the mass transit time.

13. The method of claim 12, wherein the at least one parameter further includes a heart rate of the user.

14. The method of claim 9, wherein the reference monitor comprises an inflatable cuff.

* * * * *

UNITED STATES PATENT AND TRADEMARK OFFICE
CERTIFICATE OF CORRECTION

PATENT NO. : 11,185,237 B2
APPLICATION NO. : 15/912952
DATED : November 30, 2021
INVENTOR(S) : Peters et al.

It is certified that error appears in the above-identified patent and that said Letters Patent is hereby corrected as shown below:

In the Claims

In Claim 6, at Column 9, Line 4: "The method of 1" should read --The method of claim 1--.

Signed and Sealed this
Sixth Day of September, 2022

Katherine Kelly Vidal
*Director of the United States Patent and Trademark Office*